United States Patent
Cappelletti

(10) Patent No.: US 10,265,179 B2
(45) Date of Patent: Apr. 23, 2019

(54) ADJUSTABLE MODULAR SPACER DEVICE FOR THE ARTICULATION OF THE KNEE

(71) Applicant: Ava Cappelletti, Cesena (IT)

(72) Inventor: Ava Cappelletti, Cesena (IT)

(73) Assignee: COSSINGTON LIMITED, Kingston Upon Thames, Surrey (GB)

( * ) Notice: Subject to any disclaimer, the term of this patent is extended or adjusted under 35 U.S.C. 154(b) by 0 days.

(21) Appl. No.: 14/917,146

(22) PCT Filed: Sep. 9, 2013

(86) PCT No.: PCT/IT2013/000235
§ 371 (c)(1),
(2) Date: Mar. 7, 2016

(87) PCT Pub. No.: WO2015/033361
PCT Pub. Date: Mar. 12, 2015

(65) Prior Publication Data
US 2016/0206434 A1    Jul. 21, 2016

(51) Int. Cl.
*A61F 2/38* (2006.01)
*A61F 2/30* (2006.01)

(52) U.S. Cl.
CPC ........ *A61F 2/3836* (2013.01); *A61F 2/30724* (2013.01); *A61F 2/38* (2013.01); *A61F 2/389* (2013.01); *A61F 2/3859* (2013.01); *A61F 2002/30331* (2013.01); *A61F 2002/30426* (2013.01); *A61F 2002/30449* (2013.01); *A61F 2002/30604* (2013.01); *A61F 2002/30616* (2013.01); *A61F 2002/30672* (2013.01); *A61F 2002/30677* (2013.01); *A61F 2002/3895* (2013.01); *A61F 2240/001* (2013.01); *A61F 2310/00353* (2013.01)

(58) Field of Classification Search
CPC .......... A61F 2/38; A61F 2/3836; A61F 2/385; A61F 2/30742; A61F 2/384; A61F 2002/30649; A61F 2002/3863; A61F 2002/30331; A61F 2002/30316; A61B 2017/568
See application file for complete search history.

(56) References Cited

U.S. PATENT DOCUMENTS

| | | | |
|---|---|---|---|
| 2004/0054417 A1 | 3/2004 | Soffiati et al. | |
| 2006/0190086 A1* | 8/2006 | Clemow ................... | A61F 2/38 623/20.15 |

FOREIGN PATENT DOCUMENTS

| | | |
|---|---|---|
| FR | 2780636 | 1/2000 |
| WO | 2013/041905 | 3/2013 |

* cited by examiner

Primary Examiner — Dinah Baria
(74) Attorney, Agent, or Firm — Duane Morris LLP; Gregory M. Lefkowitz; Jason M. Nolan

(57) ABSTRACT

Adjustable modular spacer device for the articulation of the knee including a tibial component, suitable for being fixedly connected to one end of the tibial bone near to the articulation of the knee, a femoral component, suitable for being fixedly connected to one end of the femoral bone near to the articulation of the knee and suitable for coming into contact and for being articulated with the tibial component, in which the femoral component includes at least one condylar articular portion and an intercondylar central body, in which the intercondylar central body and the at least one condylar articular portion are separate and discrete components of the femoral component.

25 Claims, 4 Drawing Sheets

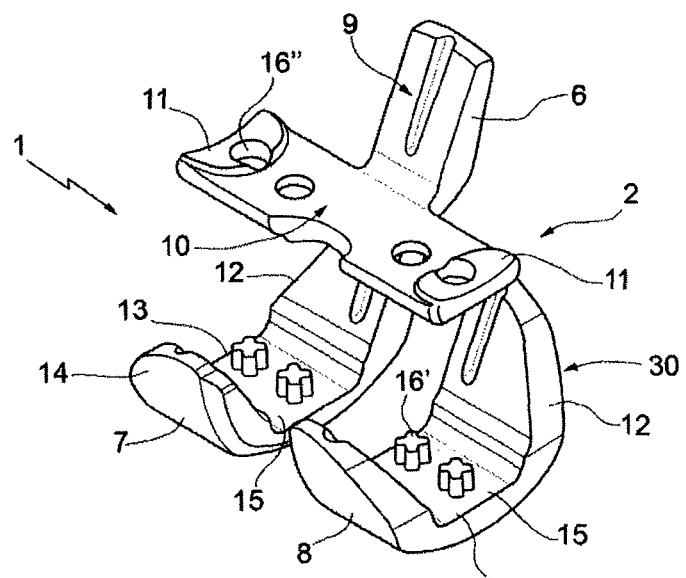
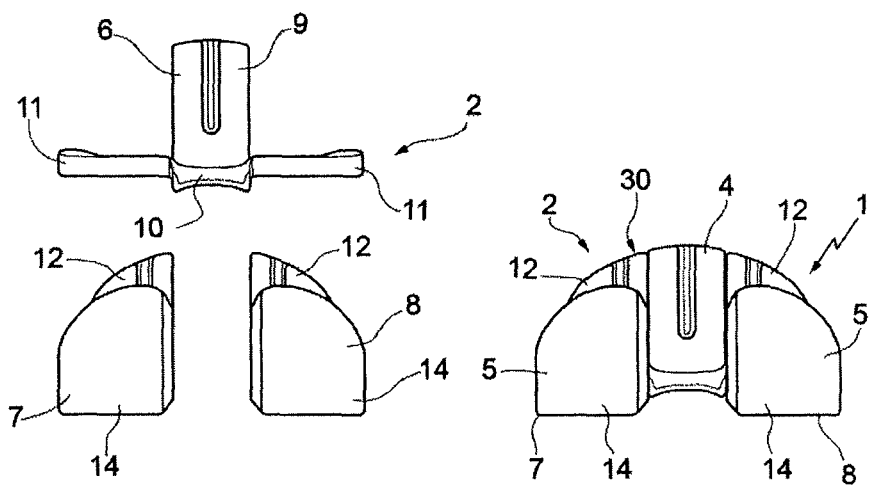
FIG.1
FIG.2
FIG.3

ADJUSTABLE MODULAR SPACER DEVICE FOR THE ARTICULATION OF THE KNEE

CROSS-REFERENCE TO RELATED APPLICATIONS

This application is a § 371national stage entry of International Application No. PCT/IT2013/000235, filed Sep. 9, 2013, the entire content of which is incorporated herein by reference.

TECHNICAL FIELD OF THE INVENTION

The present invention refers to an adjustable modular spacer device for the temporary replacement of knee joint prostheses. Such prostheses may have to be removed for different reasons, for example following an infection.

The adjustable modular spacer device makes it possible to determine the actual anatomy of the patient so as to keep the joint space necessary for implanting a new prosthesis and allowing the patient to maintain good movement of the articulation itself and the possibility of walking and moving for all the time necessary to treat the articulation or for the time from when the prosthesis is removed until the following one is implanted.

PRIOR ART

In the field of implantology of articular prostheses it is known that such devices may have to be removed for many different reasons, in particular, due to local infections of the articulation that arise after implanting the prosthesis itself.

In such a case, after removing the first prosthesis, it is necessary to treat the seats of the articulation with suitable antibiotic medication, before being able to implant the new prosthesis.

During the treatment period it is fundamental to keep the articular space necessary for implanting a new prosthesis, so as to avoid shortening of the tissues, atrophy of the joint and loss of muscle tone.

Such a technique is known as "two-stage implantation" of articular prostheses.

On the market there are temporary joint spacers for the knee, generally made from bone cement, that are capable of performing such a function.

Some of these are made manually directly during surgery for implanting the spacer itself, by the surgeon, who suitably shapes the material with which it is made according to the dimensions and to the shape of the site of the implantation.

One drawback of such spacers, however, consists of the fact that making such a device during surgery indeed increases the length of the operation, the difficulty for the surgeon, who must have good manual skills and experience, and the risk of contamination of the device when being made.

Moreover, manually made spacers can have defects that can also reduce the mobility of the treated articulation.

On the market, it is furthermore possible to find spacers for the articulation of the knee that are preformed and, therefore, immediately ready for implantation. Such spacers have two corresponding articular sides, both on the femoral component and on the tibial component, that are suitable for being articulated with one another.

However, the size and the shape of such devices are pre-established, and there is not, therefore, the possibility of perfectly adapting them at the site of implantation, especially in the case in which there is the need to replace prostheses of different sizes and types, or when there are defects or anomalies present at the site itself.

Consequently, since it is not possible to adapt such spacers to the anthropomorphic dimensions of the knee of the patient, it is more difficult to ensure good mobility of the articulation and, therefore, a good quality of life for the patient during the period in which he is waiting for a new articular prosthesis to be implanted. Alternatively, it is necessary to resect more portions of bone than those that are strictly necessary.

DISCLOSURE OF INVENTION

One purpose of the present invention is to improve the state of the art.

A further purpose of the present invention is to provide an adjustable modular spacer device for the articulation of the knee that is preformed and, at the same time, that can be adapted to the actual conditions of the articulation of the knee in which they are to be implanted.

A further advantage of the present invention is to provide an adjustable modular spacer device for the articulation of the knee that can be adapted to the different and actual anatomical dimensions of the articulation in which it is implanted, considering also the amount of bone tissue that is resected following the removal of the infected articular prosthesis.

A further purpose of the present invention is to provide an adjustable modular spacer device for the articulation of the knee that ensures high mobility and stability of the articulation itself.

Yet a further purpose of the present invention is to provide an adjustable modular spacer device for the articulation of the knee that ensures that the patient has a good quality of life once the device itself has been implanted.

In accordance with one aspect of the present invention, it is foreseen for there to be an adjustable modular spacer device for the articulation of the knee according to the attached claim 1.

The present invention further refers to a method for assembling an adjustable modular spacer device for the articulation of the knee according to the attached claim 24.

The present invention moreover refers to a group of components for an adjustable modular spacer device for the articulation of the knee according to the attached claim 27.

The dependent claims refer to preferred and advantageous embodiments of the invention.

BRIEF DESCRIPTION OF DRAWINGS

Further characteristics and advantages of the present invention shall become clearer from the detailed description of a preferred, but not exclusive, embodiment, of an adjustable modular spacer device for the articulation of the knee, illustrated as an example, but not for limiting purposes, in the attached tables of drawings, in which:

FIG. 1 is a perspective side view of a femoral component of the adjustable modular spacer device according to the present invention in a version that is not assembled;

FIG. 2 is a front view of the femoral component of the device according to FIG. 1;

FIG. 3 is a front view of the femoral component of the device according to FIGS. 1 and 2 in an assembled version;

EMBODIMENTS OF THE INVENTION

Figure 4:
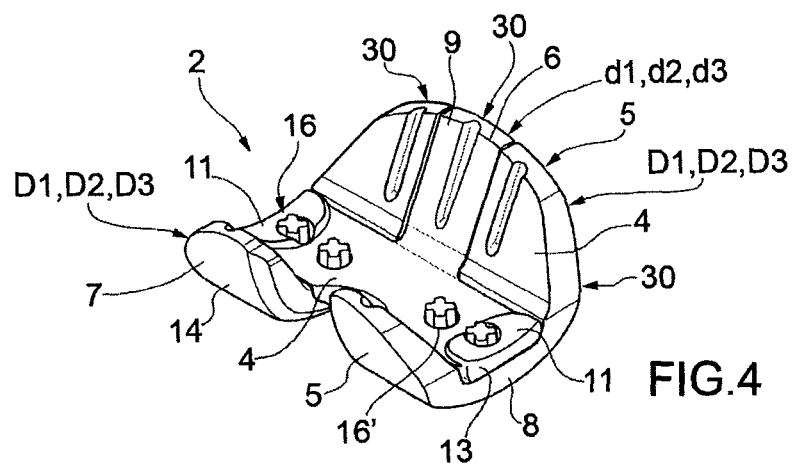
FIG. 4 is a perspective view of the assembled femoral component of FIG. 3.

The human body can be divided into regions according to planes which ideally pass through it, according to the following terminology.

The "sagittal planes" are bilateral symmetry planes that run from front to back and divide the body into two parts, right and left. They comprise a median sagittal plane, which divides the human body into two substantially symmetrical parts, and planes that are parallel to it, called lateral sagittal planes. Therefore, a position or a direction, relative to the human body, can be defined "median" or "medial", if it is at the median sagittal plane, "lateral", if it is closer to the lateral sagittal plane.

There are then "coronal" planes, which run perpendicular to the sagittal planes.

Finally, the "transverse" planes are the ones which run perpendicular to both the sagittal and coronal planes.

Analogously, it is possible to define the "anatomical axes". The main axes are: "longitudinal" or vertical, which is perpendicular to the ground, when the body is in the erect position; "transverse" or horizontal, which is directed from left to right (or vice versa) and is perpendicular to the longitudinal axis; "sagittal" or front-back, which is directed from the back surface to the front surface of the body (or vice versa). This axis is perpendicular to the other two axes.

The terms "front", "back", "vertical" or "horizontal", "lower" or "upper", used in the rest of the description, refer to the directions taken up by the human body in the erect position.

The articulation of the knee involves the following bone structure: distal epiphysis of the femur, proximal epiphysis of the tibia and patella; the articular surfaces are represented by the femoral condyles and by the relative tibial resting bases.

The distal epiphysis of the femur is made up of two condyles, medial and lateral, which join together at the front to then form the diaphysis, whereas at the back they diverge laterally; the space that is obtained is the intercondylar fossa. At the front of the distal epiphysis there is a flat triangular area, the patellar surface that is articulated with the patella, such a surface is transversally concave and vertically convex.

The articular surface of the femur, consisting of the lower surface of the two condyles is flat and is "U"-shaped, it is articulated with the tibial plateau, i.e. the upper surface of the proximal epiphysis of the tibia.

With reference to the attached figures, reference numeral 1 generically indicates an adjustable modular spacer device for the articulation of the knee.

Such a spacer can be used, as described in greater detail in the rest of the description, to replace infected articular prostheses for the knee, both of the hemi-condylar type and of the complete type, and in particularly serious cases, in which it is necessary to carry out important surgery on the articulation of the knee of certain patients. The advantage of such an adjustable modular spacer device consists of the fact that the surgeon, at the moment of implantation, after having evaluated the actual conditions of the articulation on which he is operating, can select and assemble such a device according to the actual requirements, as shall become clearer in the rest of the description.

Such an adjustable modular spacer device 1 exclusively comprises a femoral component 2 and a tibial component 3. The femoral component 2 is suitable for being fixedly connected to the end of the femoral bone near to the articulation of the knee. The tibial component 3 is suitable for being fixedly connected to the end of the tibial bone at the articulation of the knee.

There are no patellar components, since the adjustable modular spacer device 1 according to the present invention, being indeed a temporary device, has the further purpose of reducing the complexity of the implant and in order to carry out its therapeutic function, since it is in the human body for a short time, it is not necessary for it to comprise also a component that replaces the patella, as occurs on the other hand in permanent prostheses. The femoral component 2 and the tibial component 3 are suitable for coming into contact and for moving with respect to one another, reproducing the articulation of the knee of the patient.

The femoral component 2, and possibly the tibial component 3, each comprise at least two separate portions that are assembled together, so as to adapt to the dimensions of the bone ends to which they are connected, as explained in further detail in the rest of the description. Indeed, thanks to such a characteristic, the adjustable modular spacer device 1 can be used as a hemi-condylar spacer, that is to say it only has one medial or lateral articulation surface, or as a complete spacer, that is to say with both articulation surfaces, lateral and medial. Indeed, it is the surgeon, at the moment of implantation, who assembles the various parts that make up the femoral component 2 and/or the tibial component 3, based upon the actual surgical and anatomical requirements.

The femoral component 2, as visible in FIGS. 3 and 4, in an assembled version, is overall substantially "U"-shaped, comprising a concave inner surface 4, which is in contact with the bone seat, and a convex outer surface 5, which is suitable for coming into contact with the tibial component 3.

The inner surface 4 is fixedly connected to the end of the femur with which it comes into contact through the bone cement.

FIGS. 1 and 2 illustrate one non-assembled version of the femoral component 2. Such a femoral component 2 comprises an intercondylar central body 6 and at least one condylar articular portion 7, 8. In one version of the invention, the femoral component 2 comprises two condylar articular portions 7 and 8, one of which is arranged medially and the other one of which is arranged laterally with respect to the intercondylar central body 6.

The inner surface 4 of the femoral component 2 is formed by the intercondylar central body 6 and by the at least one condylar articular portion 7, 8.

The outer surface 5 of the femoral component 2 is formed by the at least one condylar articular portion 7, 8.

The intercondylar central body 6 is substantially "L"-shaped, having a first vertical arm 9 and a second horizontal arm 10, which are substantially perpendicular to one another.

The first vertical arm 9 substantially corresponds to the front space between the femoral condyles.

The second horizontal arm 10 corresponds to the space between the femoral condyles, substantially relative to the intercondylar fossa.

Therefore, the first arm 9 extends along the longitudinal or vertical axis of the human body.

The second arm 10 extends along the sagittal axis of the human body and lies along a transverse plane of the human body.

At least one extension 11 extends outwards from the second horizontal arm 10, along the transverse axis of the human body, in a lateral and/or medial manner, wherein said extension 11 lies substantially on the same transverse plane as the arm 10 from which it branches off. In one version of the invention, there are two extensions 11, one of which is positioned laterally and one of which is positioned medially with respect to the central body 6 or to its second horizontal arm 10.

The intercondylar central body 6 and the condylar articular portions 7, 8 are separate portions of the femoral component 2, but they can be associated with one another so as to form a single body, as shall be described in greater detail in the rest of the description.

The at least one condylar articular portion 7, 8 is positioned laterally and/or medially with respect to the central body 6 and substantially corresponds to the femoral condyles and to the articular surface formed by them.

The at least one condylar articular portion 7, 8 is substantially "U"-shaped, having a front portion 12, a central portion 13 and a back portion 14.

The front portion 12 of the at least one condylar articular portion 7, 8 has a vertical extension that substantially corresponds to that of the plane of the first vertical arm 9 of the central body 6, that is to say along the sagittal plane of the human body. The front portion 12 lies on a front plane of the human body.

The central portion 13 substantially lies on the same plane as the second horizontal arm 10 of the central body 6, that is to say on a transverse plane of the human body.

The front portion 14 substantially corresponds to the back surface of the femoral condyles.

One part of the intercondylar central body 6 and one part of the at least one condylar articular portion 7, 8 constitutes a front surface 30 of the device, substantially corresponding to the front surface of the femoral end. In particular, such a front surface 30 is made up of the front portion 12 of the at least one condylar articular portion 7, 8 and of the first vertical arm 9 of the intercondylar central body 6.

In the central portion 13 of the at least one condylar articular portion 7, 8 there is at least one seat 15. Such a seat 15 corresponds to the extension 11 of the central body 6 and constitutes one housing. In such a way, the extension 11 is housed in the seat 15, determining the assembly of the femoral component 2 of the adjustable modular spacer device 1 according to the present invention.

The at least one seat 15 is positioned in the central portion 13, at the inner surface 4 of the femoral component 2. Therefore, such an inner surface 4 is made up of the intercondylar central body 6, the front portion 12 and the rear portion 14 of the at least one condylar articular portion 7, 8. The fact that the seat 15 is positioned on the inner surface 4 of the femoral component 2, and that the extension 11 is housed on it, makes it possible to have an optimal adhesion of the bone cement, which is used for fixing the femoral component 2 to the relative bone portion, also in the part of connection of the intercondylar central body 6 and of the at least one condylar articular portion 7, 8. Moreover, this also promotes the correct articulation of the knee, since the outer surface 5 of the articulation with the tibial component 3 is smooth, without level differences or asperity and it is, especially, continuous and without interruptions.

Between the seat 15 and the extension 11 there are some interlocking fastening means 16, that are capable of connecting and joining the condylar articular portions 7, 8 to the intercondylar central body 6.

The surgeon, indeed, as mentioned previously, selects the various parts of the femoral component 2, assembling them together, so as to make an adjustable modular spacer device 1 that best adapts to the dimensions of the articulation to be treated and to the specific surgery requirements of the patient.

In one version of the invention, such interlocking fastening means are of the removable type.

In one version of the invention, such interlocking fastening means 16 are in the form of protrusions 16' that can be inserted in corresponding holes 16".

Alternatively, the interlocking fastening means 16 can be any known means suitable for fastening to a corresponding further means, so as to create a connection between two components, that is to say bayonet coupling means, mechanical fastening means, removable mechanical fastening means, etcetera.

In one version of the invention, the interlocking fastening means 16 present in the condylar articular portion 7, for example in the lateral position, and in the relative extension 11, differ from the interlocking fastening means 16, present in the condylar articular portion 8, for example in the medial position, and in the relative extension 11.

In such a way, during implantation, a condylar articular portion, for example in the lateral position, can be univocally coupled to the relative extension, avoiding any possibility of error when assembling the femoral component 2.

Once it has been assembled, the peripheral surfaces of the central body 6 and of the articular portions 7, 8 are level and, therefore, perfectly match, so as to obtain a femoral component that is similar to those preformed in a single piece, known on the market.

In order to promote modularity of the adjustable modular spacer device 1, the at least one extension 11 and the at least one seat 15 have the same dimensions and coupling modalities, despite the fact that the size of the femoral component 2 can be selected so as to respond to the necessity of the surgeon and to the anatomy of the place of implantation, as shall be described in the rest of the description.

The at least one condylar articular portion 7, 8 has a size D1 or D2 or D3. In particular, the size D1 is smaller than D2, which in turn is smaller than D3. The surgeon, during implantation, can select the size D1 or D2 or D3 according to the real necessities of the patient. Therefore, the at least one condylar articular portion 7, 8 has differentiated sizes so as to be able to be selected according to the size and to the shape of the articulation of the knee.

All the sizes of the articular portions 7, 8 are associated with the central body 6 through the interlocking fastening means 16, so as to achieve a perfect coupling and assembly of the femoral component 2.

In such a way, the femoral component 2 is modular, since it is made up of many parts, and adjustable, since it is possible, by replacing a component and selecting one with a more adequate size, to adapt in the best way possible to the anatomical requirements of the patient.

Figure 5:
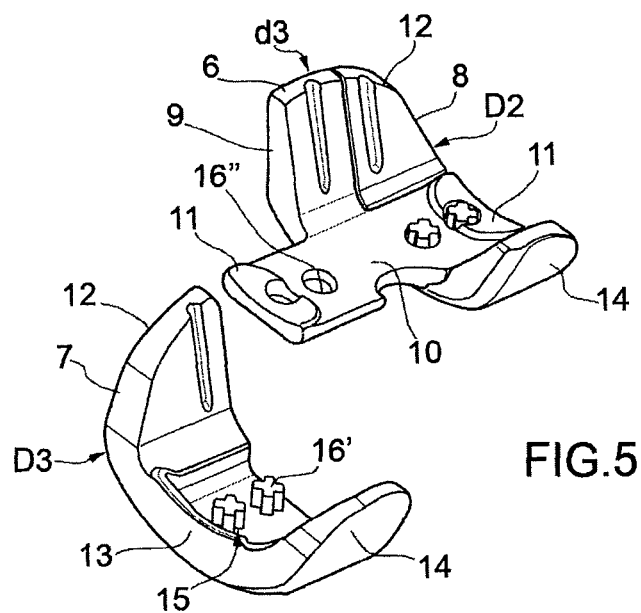
FIG. 5 is a perspective side view of a further version of the femoral component of the adjustable modular spacer device according to the present invention in a partially assembled version.

Moreover, it is possible to select a size for the articular portion 7 that differs from the size of the articular portion 8, according to the specific requirements, as illustrated as an example in FIG. 5.

In one version of the invention, the central body 6 can also have a size d1, or d2 or d3, in which d1 is smaller than d2 that in turn is smaller than d3.

Given that the interlocking fastening means 16 have the same dimensions and the same configuration, any size of intercondylar central body 6 can be assembled on any size of the at least one condylar articular portion 7, 8. Therefore, the intercondylar body 6 has differentiated sizes so as to be able to be selected according to the size and to the shape of the articulation of the knee.

Therefore, the surgeon, after having selected the portions of femoral component 2 that are necessary for implantation, can further choose their optimal size and assemble the whole thing, thus obtaining the assembled femoral component 2 that best suits the specific requirements.

The tibial component 3 of the adjustable modular spacer device 1 corresponds to a tibial plateau, on which the femoral component 2 described above is articulated.

The tibial component 3 comprises an intercondylar central element 17 and at least one condylar articular base 18, 19. In one version of the invention, there are two articular condylar bases 18, 19.

Figure 6:
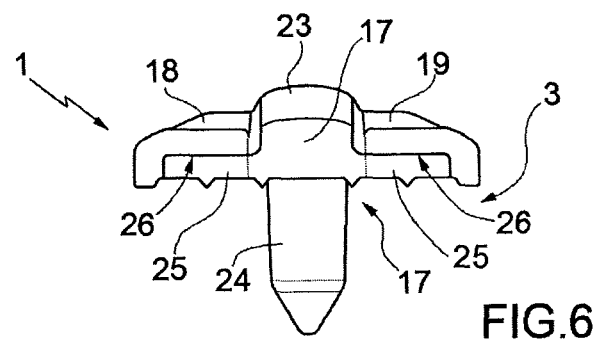
FIG. 6 is a front view of a tibial component of the adjustable modular spacer device according to the present invention in an assembled version.
Figure 9:
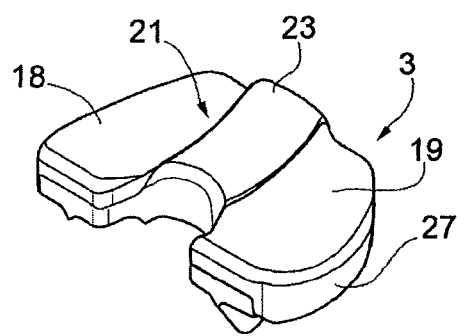
FIG. 9 is a perspective side view of the assembled tibial component according to FIG. 6.
Figure 10:
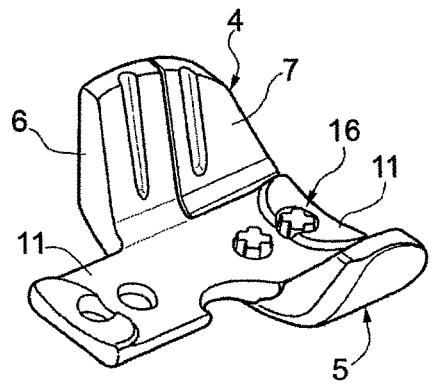
FIG. 10 is a perspective side view of an embodiment of the femoral component of the adjustable modular spacer device according to the present invention in an assembled version.

The tibial component 3, as visible in FIGS. 6 and 9, in one assembled version, overall has an upper surface 21, that is slightly concave, in articulation with the outer surface 5 of the femoral component 2, and a lower surface, in contact with the bone seat.

The lower surface is fixedly connected to the end of the tibia with which it comes into contact through the bone cement, both directly and, possibly, through the interposition of a further tibial component (not illustrated).

Figure 7:
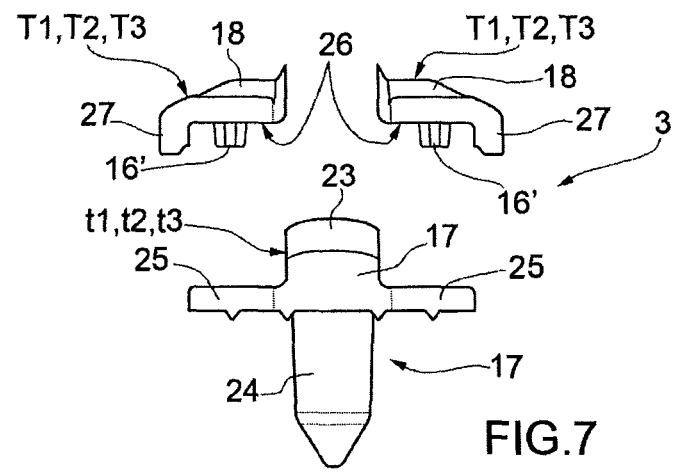
FIG. 7 is a front view of the tibial component according to FIG. 6, in a version that is not assembled.
Figure 8:
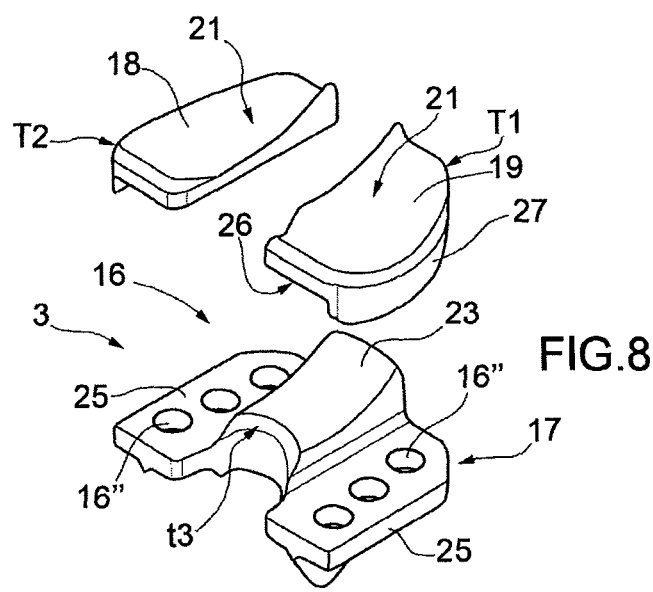
FIG. 8 is a perspective side view of the non-assembled tibial component of FIG. 7.

FIGS. 7 and 8, illustrate a version of the tibial component 3 that is not assembled.

The intercondylar central element 17 corresponds to the intercondylar space or to the second horizontal arm 10 of the intercondylar central body 6 of the femoral component 2. The intercondylar central element 17 substantially lies on a transverse plane of the human body and extends parallel to the sagittal axis of the human body.

The intercondylar central element 17 can comprise a protrusion 23, in the front portion thereof, that is suitable for improving the articulation with the femoral component 2 and for limiting the possibility of rotation between them.

A pin 24 projects from the intercondylar central element 17, in particular from its lower surface. Such a pin 24 extends substantially vertically, that is to say it is parallel to the longitudinal axis of the human body. Such a pin 24 is implanted in the tibial bone so as to stabilise the implantation of the tibial component 3 of the adjustable modular spacer device 1 according to the present invention.

The intercondylar central element 17 and the at least one condylar articular base 18, 19 are separate portions of the tibial component 3, but can be connected and associated to one another so as to form a single body, as shall be described in greater detail in the rest of the description.

The at least one condylar articular base 18, 19 is positioned laterally and/or medially with respect to the intercondylar central element 17 and substantially corresponds to the ground and rotation base, present on the tibial plateau, of the femoral condyles or of the at least one condylar articular portion 7, 8 of the femoral component 2.

The surface of the articular bases 18, 19, corresponding to the upper surface 21, is slightly concave, so as to correspond to the convex surface of the articular portions 7, 8 of the femoral component.

The upper surface 21 is formed by the at least one condylar articular base 18, 19 and by the intercondylar central element 17.

The lower surface is formed by the intercondylar central element 17.

At least one second extension 25 substantially lying on the transverse plane of the human body projects outwards from the intercondylar central element 17 along the transverse axis of the human body, in a lateral and/or medial manner.

Each condylar articular base 18, 19 has at least one seat 26 that is suitable for housing the at least one second extension 25.

In particular, such at least one seat 26 is positioned in the lower part of the condylar articular base 18, 19, in the resting surface of the base itself on the at least one second extension 25 of the central element 17 of the tibial component 3. By housing the at least one second extension 25 in the at least one seat 26, the tibial component 3 of the adjustable modular spacer device 1, according to the present invention, is assembled.

Between the seat 26 and the second extension 25 there are interlocking fastening means 16, that are capable of fastening the articular condylar bases 18, 19 to the central element 17.

The surgeon, indeed, as previously mentioned, selects the various parts of the tibial component 3, assembling them together, so as to obtain an adjustable modular spacer device 1 that best adapts to the size of the articulation to be treated and to the specific surgical requirements of the patient.

Such interlocking fastening means, in one version of the invention, are of the removable type.

In one version of the invention, such interlocking fastening means 16 are in the form of protrusions 16' which can be inserted into corresponding holes 16".

Alternatively, the interlocking fastening means 16 can be any known means suitable for fastening a corresponding further means, so as to create a connection between two components, such as a bayonet coupling means, a mechanical hooking means, a removable mechanical hooking means, etcetera.

In one version of the invention, the interlocking fastening means 16 present in the condylar articular base 18, for example in the lateral position, and in the relative second extension 25, differ from the interlocking fastening means 16, present in the condylar articular base 19, for example in the medial position, and in the relative second extension 25.

In such a way, during implantation, an articular base, for example in the lateral position, can be univocally coupled with the relative second extension, so as to avoid any possibility of error during assembly of the tibial component 3.

Once it has been assembled, the peripheral surfaces of the intercondylar central element 17 and of the articular condylar bases 18, 19 match, so as to achieve a tibial component that is similar to those preformed in a single piece, known on the market.

Analogously to what has been described above, in order to promote the modularity of the adjustable modular spacer device 1, the second extension 25 and the seat 26 maintain the same dimensions and coupling modalities, despite the fact that the sizes of the tibial component 3 can be selected so as to respond to the requirements of the surgeon and to the anatomy of the place of implantation, as described in detail in the rest of the description.

Therefore, the surgeon, after having selected the portions of femoral component 2 that are necessary for the implantation, can further establish their optimal size and assemble the whole thing obtaining the assembled femoral component 2 that is most adequate for the specific requirements.

The articular condylar bases 18, 19 have a shoulder 27, in their lateral or medial ends. Such a shoulder projects from the transverse plane of the articular base 18, 19 towards the portion of the tibial bone, covering the side of the at least one second extension 25. Such a shoulder 27 makes it possible for any size or dimension of condylar articular base 18, 19, as described in greater detail in the rest of the description, to house the second extension 15, present in any size of intercondylar central element 17, as shall be described in greater detail in the rest of the description. Indeed, the size of the extension 11, or of the second extension 25, and of the seat 15, or of the second seat 26, in addition to being the size of the interlocking fastening means 16, are the same for any size of intercondylar central body 6, condylar articular portions 7, 8 or central condylar element 17 and articular condylar bases 18, 19, in order to be able to select them based upon real needs of the patient, and especially, so as to be able to allow them to be coupled with any further size of the different components of the adjustable modular spacer device 1 according to the present invention.

Indeed, the condylar articular base 18, 19 has a size T1 or T2 or T3. In particular, the size T1 is smaller than T2, which in turn is smaller than T3. The surgeon, at the moment of implantation, can select the size T1 or T2 or T3 according to the real needs of the patient. All the sizes of the articular condylar bases 18, 19 are associated with the intercondylar central element 17 through the interlocking fastening means 16, so as to achieve a coupling and assembly of the tibial component 3. Therefore, the intercondylar central element 17 has differentiated sizes so as to be selectable according to the size and to the shape of the articulation of the knee.

In such a way, the tibial component 3 is modular, since it is made up of many parts, and adjustable, since it is possible, by replacing a component and by selecting one with a more correct size, to adapt in the best way possible to the anatomical requirements of the patient.

Moreover, it is possible to select a size for the condylar articular base 18 that differs from the size of the condylar articular base 19, according to the specific requirements.

In one version of the invention, the intercondylar central element 17 can also have a size t1, or t2 or t3, in which t1 is smaller than t2 which in turn is smaller than t3.

Given that the interlocking fastening means 16 have the same dimensions and the same configuration, any size of intercondylar central element 17 can be assembled to any size of articular condylar bases 18, 19. Therefore, the at least one condylar articular base 18, 18 has differentiated sizes so as to be selectable according to the size and to the shape of the articulation of the knee.

The interlocking fastening means 16, once the correct sizes and shapes of the adjustable modular spacer device 1 have been established, are fixed with bone cement or other material that is suitable for the purpose.

The femoral component 2 and the tibial component 3 are preformed and made entirely from biologically compatible material.

Such biologically compatible material is porous.

Such biologically compatible material can be selected from metals, metal alloys, organometallic compounds, ceramics, resins having high porosity, plastic materials and/or a combination of these.

Specifically, the aforementioned plastic materials can be selected from thermoplastic polymers, such as acrylic resins, polyethylene, polypropylene, polyester, thermoformable polymers and other similar materials.

In one version of the present invention, the biologically compatible material is a bone cement, for example polymethylmethacrylate (PMMA).

The aforementioned biologically compatible material, thanks to its porosity, can be impregnated with pharmaceutical and/or therapeutic products.

The impregnation of the biologically compatible material with pharmaceutical and/or therapeutic products can be directly carried out by the manufacturer or by the surgeon before implantation. Moreover, the surgeon, according to the specific requirements of the patient, can impregnate with a second pharmaceutical and/or therapeutic product an adjustable modular spacer device 1 that has already been previously impregnated by the manufacturer with a first pharmaceutical and/or therapeutic product that is different from the second one.

In one further embodiment, the biologically compatible material can be added with at least one pharmaceutical and/or therapeutic product during the manufacturing of the adjustable modular spacer device 1.

The porosity of the material with which the adjustable modular spacer device 1 is made can be selected so as to release the pharmaceutical and/or therapeutic substances over a long period of time at low concentrations, or with higher concentrations over shorter periods of time. In such a way, the specific requirements of the patient can be satisfied.

Of course, each portion or component of the adjustable modular spacer device 1 can be loaded with a specific pharmaceutical and/or therapeutic product, according to the requirement, or at the same time be free of such substances.

Moreover, in the case in which only one part of the articulation of the knee is damaged, or again in the case in which there is a localised infection, the surgeon can decide to select and use only the femoral component 2 or the tibial component 3 of the adjustable modular spacer device 1.

Moreover, in the case in which the damage of the articulation of the knee is hemi-condylar, or in the case in which a hemi-condylar prosthesis is replaced, that is to say only concerning the lateral or medial area thereof, or again in the case in which there is a localised infection, it is possible to select only the necessary components, that is to say only one of the condylar articular portions 7, 8 or only one of the articular condylar bases 18, 19, as illustrated as an example, in FIGS. 10-13; in such a way the surgeon who selects the components and sizes of the various parts of the adjustable modular spacer device 1 can do this by carrying out a specific evaluation before implanting the device itself.

Figure 11:
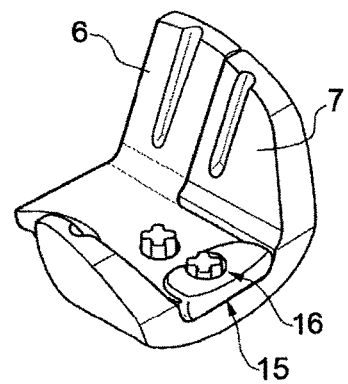
FIG. 11 is a perspective side view of a further embodiment of the femoral component of the adjustable modular spacer device according to the present invention in an assembled version.
Figure 12:
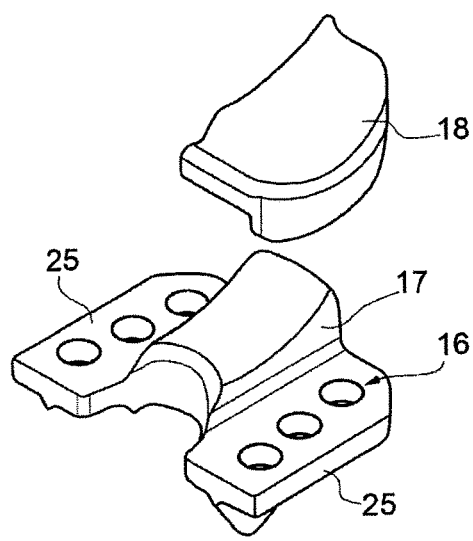
FIG. 12 is a perspective side view of an embodiment of the tibial component of the adjustable modular spacer device according to the present invention in a version that is not assembled.
Figure 13:
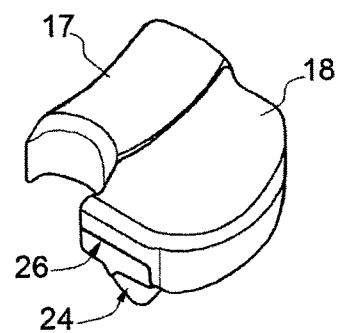
FIG. 13 is a perspective side view of a further embodiment of the tibial component of the adjustable modular spacer device according to the present invention in an assembled version.

Even in such a case, it is possible to use the desired size of such portions and, then, assemble the whole thing. The possible extension 11, or second extension 25, not used since the corresponding portion of the articulation of the knee is not involved in the implant, can be removed by the surgeon through cutting with normal surgical instruments. Alternatively, the intercondylar central body 6 and/or the intercondylar central element 17 can be foreseen only with an extension 11 and/or a second extension 25, according to the requirements. Examples of such embodiments are illustrated in FIGS. 11 and 13.

Finally, it is possible for there to be, at the connection joints between the extension 11 and the intercondylar central body 6 and/or between the second extension 25 and the intercondylar central element 17, separation means or precuts, so as to facilitate the separation of the portions that are not used and not necessary for the surgeon.

The femoral component 2 and the tibial component 3, in the surfaces 4 and 22 of contact with the respective bone tissues, comprise at least one groove that makes it possible to obtain a better adhesion of the bone cement.

The presence of such at least one groove makes it possible to contain and hold the bone cement, preventing the latter from becoming dispersed or flow off during the adhesion step of the femoral component 2 or of the tibial component 3 with the relative bone tissue.

The present invention further comprises a method for assembling an adjustable modular spacer device 1 for the articulation of the knee comprising exclusively a femoral component 2 and a tibial component 3, in which the femoral component 2 is suitable for being fixedly connected to one end of the femoral bone near to the articulation of the knee, in which the tibial component 3 is suitable for being fixedly connected to one end of the tibial bone near to the articulation of the knee, the femoral component 2 being suitable for coming into contact and for being articulated with the tibial component 3, comprising a step of providing a femoral component 2 comprising an intercondylar central body 6 and at least one condylar articular portion 7, 8, in which the at least one condylar articular portion 7, 8 has a size D1 or D2 or D3, in which the size D1 is smaller than D2 and the size D2 is smaller than D3 and/or in which the intercondylar central body 6 has a size d1, or d2 or d3, in which d1 is smaller than d2 and d2 is smaller than d3.

The method according to the present invention comprises a step of selecting the size D1 or D2 or D3 of the at least one condylar articular portion 7, 8 and the size d1, or d2 or d3 of the intercondylar central body 6.

Subsequently there is a step of associating the selected size of the at least one condylar articular portion 7, 8 with the selected size of said intercondylar central body 6; there is also a step of assembling the femoral component 2.

Alternatively to or in combination with the steps mentioned above, the method according to the present invention comprises a step of arranging a tibial component 3 comprising at least one condylar articular base 18, 19 and an intercondylar central element 17, in which the at least one condylar articular base 18, 19 has a size T1 or T2 or T3, in which the size T1 is smaller than T2 and the size T2 is smaller than T3 and in which the intercondylar central element 17 has a size t1, or t2 or t3, in which t1 is smaller than t2 and t2 is smaller than t3.

The method according to the present invention comprises a step of selecting the size T1 or T2 or T3 of the at least one condylar articular base 18, 19 and the size t1, or t2 or t3 of the intercondylar central element (17). There is then a step of associating the selected size of the at least one condylar articular base 18, 19 with the selected size of the intercondylar central element 17 and a step of assembling the tibial component (3).

The method according to the present invention further comprises the steps of arranging the intercondylar central body 6 provided with at least one extension 11, arranging the at least one condylar articular portion 7, 8 provided with at least one seat 15, inserting the at least one extension 11 in the at least one seat 15, connecting the at least one extension 11 and the at least one seat 15 through interlocking fastening means 16, in such a way assembling the femoral component 2.

The method according to the present invention can comprise the steps of arranging the intercondylar central element 17 provided with at least one second extension 25, arranging the at least one condylar articular base 18, 19 provided with at least one second seat 26, inserting the at least one second extension 25 in the at least one second seat 26, connecting the at least one second extension 25 and the at least one second seat 26 through interlocking fastening means 16, in such a way assembling the tibial component 3.

In order to grant the surgeon maximum freedom of choice, the intercondylar central body 6 and the condylar articular portions 7, 8 of the femoral component 2 and the intercondylar central element 17 and the articular condylar bases 18, 19 can be each packed in a separate package and in a specific size. Indeed, each size of an element of the femoral component can be coupled with any size of the other elements of the femoral component and can be articulated with any size of the tibial component and vice versa.

Moreover, the shape of the aforementioned adjustable modular spacer device 1 makes it possible to obtain high mobility of the articulation of the knee, and a movement that is similar to that of a natural articulation, in spite of having different anatomical measurements, between the different articular portions of the patient.

The possibility of pre-additiving or additiving the adjustable modular spacer device 1 with pharmaceutical and/or therapeutic products makes it moreover possible to treat many different local infections in the seat of the articulation and to reach the optimal conditions for implanting a new articular prosthesis.

The present invention refers to a group of components for an adjustable modular spacer device 1 for the articulation of the knee exclusively comprising a femoral component 2 and a tibial component 3, in which the femoral component 2 is suitable for being fixedly connected to one end of the femoral bone near to the articulation of the knee, in which the tibial component 3 is suitable for being fixedly connected to one end of the tibial bone near to the articulation of the knee, the femoral component 2 is suitable for coming into contact and for being articulated with the tibial component 3, in which the femoral component 2 comprises at least one condylar articular portion 7, 8 and an intercondylar central body 6 and/or the tibial component 3 comprises an intercondylar central element 17 and at least one condylar articular base 18, 19, in which the at least one condylar articular portion 7, 8 has a size D1 or D2 or D3, in which the size D1 is smaller than D2 and the size D2 is smaller than D3 and/or in which the intercondylar central body 6 has a size d1, or d2 or d3, in which d1 is smaller than d2 and d2 is smaller than d3, and/or in which the at least one condylar articular base 18, 19 has a size T1 or T2 or T3, in which the size T1 is smaller than T2 and the size T2 is smaller than T3 and/or in which the central element 17 has a size t1, or t2 or t3, in which t1 is smaller than t2 and t2 is smaller than t3.

The invention thus conceived can in any case undergo numerous modifications and variants all covered by the same inventive concept.

Moreover, all the details can be replaced by other technically equivalent elements. In practice, the materials used, as well as the contingent shapes and sizes, can be any according to the requirements without for this reason departing from the scope of protection of the following claims.

The invention claimed is:

1. Adjustable modular spacer device for an articulation of a knee in a human body, comprising a femoral component and a tibial component,
   wherein said femoral component is suitable for being fixedly connected to one end of a femoral bone near the articulation of the knee,
   wherein said tibial component is suitable for being fixedly connected to one end of a tibial bone near to the articulation of the knee,
   said femoral component being suitable for coming into contact and for being articulated with said tibial component,
   wherein said femoral component comprises a concave inner surface, configured to be in contact with the one end of the femoral bone, and an outer surface, suitable for coming into contact with said tibial component and for making a condylar articulation,
   wherein said tibial component comprises an upper surface, suitable for coming into contact with said femoral component and for making the condylar articulation, and a lower surface, configured to be in contact with the one end of the tibial bone,
   said femoral component comprising at least one condylar articular portion and an intercondylar central body,
   wherein said at least one condylar articular portion comprises a planar inner surface along a transverse axis of the human body and opposing said outer surface of the femoral component;
   wherein said intercondylar central body and said at least one condylar articular portion are separate portions of said femoral component, respectively,
   wherein said intercondylar central body is "L"-shaped, comprising a vertical arm corresponding to a front space between the femoral condyles, and a horizontal arm comprising at least one extension configured to extend outwardly from the horizontal arm along the transverse axis of the human body and lie on a transverse plane of the human body,
   wherein said at least one condylar articular portion comprises at least one seat configured to receive the at least one extension of said horizontal arm of said intercondylar central body, and
   wherein said at least one seat is positioned on a central portion of the at least one condylar articular portion, and on the planar inner surface.

2. Adjustable modular spacer device according to claim 1, wherein said intercondylar central body is configured to be coupled with said at least one condylar articular portion.

3. Adjustable modular spacer device according to claim 1, wherein said at least one condylar articular portion is positioned in a medial or lateral position with respect to said intercondylar central body or wherein there are two condylar articular portions in a medial or lateral position with respect to said intercondylar central body.

4. Adjustable modular spacer device according to claim 1, wherein said femoral component further comprises a cross-section, parallel to a sagittal plane of the human body that is substantially "U"-shaped.

5. Adjustable modular spacer device according to claim 1, wherein part of said intercondylar central body and part of said at least one condylar articular portion constitute a front surface of the femoral component.

6. Adjustable modular spacer device according to claim 1, wherein said at least one condylar articular portion is substantially "U"-shaped, comprising a front portion, a central portion and a rear portion.

7. Adjustable modular spacer device according to claim 6, wherein said front portion of said at least one condylar articular portion and said vertical arm of said intercondylar central body constitute a front surface of the femoral component.

8. Adjustable modular spacer device according to claim 1, wherein said concave inner surface of said femoral component comprises said intercondylar central body, said at least one extension, a front portion and a rear portion of said at least one condylar articular portion.

9. Adjustable modular spacer device according to claim 1, wherein said tibial component further comprises an intercondylar central element lying on the transverse plane of the human body, and/or an intercondylar central element comprising a pin, projecting vertically.

10. Adjustable modular spacer device according to claim 9, wherein said intercondylar central element comprises at least one second extension that extends along the transverse axis of the human body, in a lateral and/or medial manner, and lies on the transverse plane of the human body.

11. Adjustable modular spacer device according to claim 10, wherein said tibial component further comprises at least one condylar articular base that forms at least one second seat, suitable for housing said at least one second extension.

12. Adjustable modular spacer device according to claim 11, wherein said at least one condylar articular base provide one medial end or one lateral end and at least one shoulder, positioned at said medial end or said lateral end, which projects towards the one end of the tibial bone, for covering said at least one second extension.

13. Adjustable modular spacer device according to claim 11, wherein said femoral component and/or said tibial component comprise an interlocking fastener, arranged between said intercondylar central body and said at least one condylar articular portion and/or between said intercondylar central element and said at least one condylar articular base.

14. Adjustable modular spacer device according to claim 13, wherein said interlocking fastener is positioned between said at least one seat and said at least one extension of said femoral component and/or said at least one second seat and said at least one second extension of said tibial component.

15. Adjustable modular spacer device according to claim 13, wherein said interlocking fastener is removable.

16. Adjustable modular spacer device according to claim 13, wherein said femoral component comprises the interlocking fastener arranged between said intercondylar central body and said at least one condylar articular portion.

17. Adjustable modular spacer device according to claim 11, wherein said at least one condylar articular portion has a size D1 or D2 or D3,
   wherein the size D1 is smaller than the size D2 and the size D2 is smaller than D3, and/or
   wherein said intercondylar central body has a size d1, or d2 or d3, wherein d1 is smaller than d2 and d2 is smaller than d3, and/or
   wherein said at least one condylar articular base has a size T1 or T2 or T3, wherein the size T1 is smaller than T2 and the size T2 is smaller than T3 and/or
   wherein said intercondylar central element has a size t1, or t2 or t3, wherein t1 is smaller than t2 and t2 is smaller than t3.

18. Adjustable modular spacer device according to claim 1, wherein said femoral component and said tibial component are preformed and comprise a biologically compatible and porous material,
wherein said biologically compatible and porous material is selected from at least one of the following materials: metals, metal alloys, organometallic compounds, ceramics resins having high porosity, plastic materials, thermoplastic polymers, acrylic resins, polyethylene, polypropylene, polyester, thermoformable polymers, bone cement, polymethylmethacrylate (PMMA), and a combination thereof.

19. Adjustable modular spacer device according to claim 18, wherein said biologically compatible and porous material further comprises at least one pharmaceutical or therapeutic product.

20. Adjustable modular spacer device according to claim 1, wherein said femoral component and/or said tibial component comprises at least one groove in contact with the one end of femoral and/or one end of tibial bone.

21. Adjustable modular spacer device as claimed in claim 1, wherein said tibial component further comprises an intercondylar central element and at least one condylar articular base, and
wherein said intercondylar central element and said at least one condylar articular base are separate portions of said tibial component.

22. Method for assembling the adjustable modular spacer device as claimed in claim 1, comprising the following steps of:
wherein said at least one condylar articular portion has a size D1 or D2 or D3, wherein the size D1 is smaller than D2 and the size D2 is smaller than D3, and
wherein said intercondylar central body has a size d1, or d2 or d3, wherein d1 is smaller than d2 and d2 is smaller than d3,
selecting the size D1 or D2 or D3 of said at least one condylar articular portion and the size d1, or d2 or d3 of said intercondylar central body,
matching the selected size of said at least one condylar articular portion with the selected size of said intercondylar central body,
arranging the selected size of said intercondylar central body and the selected size of said at least one condylar articular portion so that said at least one extension can be inserted in said at least one seat,
inserting said at least one extension in said at least one seat, and
connecting said at least one extension and said at least one seat with an interlocking fastener, to obtain the femoral component, and
said tibial component comprises at least one condylar articular base and an intercondylar central element,
wherein said intercondylar central element comprises at least one second extension that extends along the transverse axis of the human body, in a lateral and/or medial manner, and lies on the transverse plane of the human body,
wherein said intercondylar central element comprises at least one second extension that extends along the transverse axis of the human body, in a lateral and/or medial manner, and lies on the transverse plane of the human body;
wherein said at least one condylar articular base has a size T1 or T2 or T3, wherein the size T1 is smaller than T2 and the size T2 is smaller than T3, and
wherein said intercondylar central element has a size t1, or t2 or t3, wherein t1 is smaller than t2 and t2 is smaller than t3,
selecting the size T1 or T2 or T3 of said at least one condylar articular base and the size t1, or t2 or t3 of said intercondylar central element,
matching the selected size of said at least one condylar articular base with the selected size of said intercondylar central element, and
assembling the selected size of said at least one condylar articular base and the selected size of said intercondylar central element to obtain the tibial component.

23. Method according to claim 22, wherein said intercondylar central element comprises at least one second extension, and said at least one condylar articular base comprises at least one second seat, and
wherein said assembling the selected size of said at least one condylar articular base and the selected size of said intercondylar central element comprises:
arranging said intercondylar central element and said at least one condylar articular base so that said at least one second extension can be inserted in said at least one second seat,
inserting said at least one second extension in said at least one second seat, and
connecting said at least one second extension and said at least one second seat with an interlocking fastener.

24. Kit comprising the adjustable modular spacer device as claimed in claim 1,
wherein said femoral component comprises said at least one condylar articular portion and said intercondylar central body and
said tibial component comprises an intercondylar central element and at least one condylar articular base,
wherein said at least one condylar articular portion has a size D1 or D2 or D3,
wherein the size D1 is smaller than D2 and the size D2 is smaller than D3 and/or
wherein said intercondylar central body has a size d1, or d2 or d3,
wherein d1 is smaller than d2 and d2 is smaller than d3, and/or
wherein said at least one condylar articular base has a size T1 or T2 or T3,
wherein the size T1 is smaller than T2 and the size T2 is smaller than T3 and/or
wherein said intercondylar central element has a size t1, or t2 or t3,
wherein t1 is smaller than t2 and t2 is smaller than t3.

25. Kit according to claim 24, wherein said femoral component or tibial component is packaged individually, and/or one or more of said sizes D1, D2, and D3 of said at least one condylar articular portion, or one or more of said sizes d1, d2, and d3 of said intercondylar central body, or one or more sizes T1, T2, and T3 of said at least one condylar articular base, or one or more of said sizes t1, t2, and t3 of said intercondylar central element is packaged individually.

* * * * *